United States Patent
Massaro (10) Patent No.: US 8,152,930 B2
(45) Date of Patent: Apr. 10, 2012

(54) METHOD AND APPARATUS FOR REMOVING RESIDUAL MATERIAL FROM SAMPLE PLATES

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 239 days.

(21) Appl. No.: 12/469,873

(22) Filed: May 21, 2009

(65) Prior Publication Data

US 2010/0294319 A1    Nov. 25, 2010

(51) Int. Cl.
- B08B 7/00       (2006.01)
- B08B 7/04       (2006.01)
- B08B 9/20       (2006.01)
- B08B 9/22       (2006.01)

(52) U.S. Cl. ... 134/22.18; 134/22.1; 134/32; 134/168 R; 134/168 C; 422/510

(58) Field of Classification Search .................. 134/22.1, 134/22.18, 26, 30, 34, 42, 32, 33, 133, 134, 134/135, 137, 166 R, 168 R, 168 C; 422/551, 422/552, 553, 554, 501, 510
See application file for complete search history.

(56) References Cited

U.S. PATENT DOCUMENTS

| | | | | |
|---|---|---|---|---|
| 2,546,385 A | * | 3/1951 | Christina | 134/89 |
| 2,827,063 A | * | 3/1958 | Roy | 134/171 |
| 4,021,266 A | | 5/1977 | Kitterman et al. | |
| 4,483,925 A | | 11/1984 | Noack | |
| 4,685,480 A | * | 8/1987 | Eck | 134/182 |
| 4,948,564 A | * | 8/1990 | Root et al. | 422/534 |
| 5,078,164 A | * | 1/1992 | Doellgast | 134/166 R |
| 6,403,379 B1 | * | 6/2002 | Munson et al. | 436/43 |
| 7,115,231 B1 | * | 10/2006 | Zhou et al. | 422/552 |
| 2004/0200509 A1 | | 10/2004 | Felder et al. | |

FOREIGN PATENT DOCUMENTS

WO    WO 2006/017737 A2    2/2006

OTHER PUBLICATIONS

International Search Report and Written Opinion for International Application No. PCT/US2010/001432 dated Aug. 25, 2010.

* cited by examiner

*Primary Examiner* — Alexander Markoff
(74) *Attorney, Agent, or Firm* — Wolf, Greenfield & Sacks, P.C.

(57) ABSTRACT

Method and apparatus for removing residual material from sample wells of a multiwell plate. Wells located on a multi-well plate are placed in fluid communication with wash wells of a wash reservoir where cleaning fluid is provided to remove residual material from the sample wells of the multiwell plate.

11 Claims, 7 Drawing Sheets

METHOD AND APPARATUS FOR REMOVING RESIDUAL MATERIAL FROM SAMPLE PLATES

BACKGROUND OF INVENTION

1. Field of the Invention

This invention relates to removing residual material from sample plate wells.

2. Related Art

Multiwell plates are commonly used for biological research applications, particularly cellular assays or other medically-related biochemical studies. In this respect, research studies may be conducted with high throughput since multiwell plates commonly contain 96 or more separate wells where individual experiments or other operations may be conducted. Oftentimes, once an assay is performed, an amount of material may be left in the wells. A common technique for removal of the material is to invert the plate so as to dump the contents of the wells. However, in some cases, even after inverting a plate and dumping the well contents, there remains liquid or other material at or near the rim of each well of the plate. In one technique, the remaining liquid or other material at the rim of wells is removed by contacting the well rims with a piece of filter paper to blot the leftover material away.

SUMMARY OF INVENTION

The inventor has appreciated that for some applications, removing residual material that is left over at or near the wells of multiwell plates can be difficult to do in a high throughput, efficient and/or ecologically-friendly manner. In different aspects of the present invention, a wash or cleaning fluid may be used to remove residual material from the rims of a multiwell plate, decreasing the possibility of extraneous or contaminating material being left at one or more wells and/or without requiring the use of blotting filter paper or other similar material.

In one aspect of the invention, a method for removing residual material from a plurality of wells of a multiwell plate involves providing a multiwell plate that includes a top side where wells are open to receive fluid and also includes a bottom side, e.g., where the wells are closed. A wash reservoir may be provided that has one or more wash wells arranged to correspond to wells of the multiwell plate, and a cleaning fluid may be provided at each of the plurality of wash wells. The multiwell plate may be inverted such that the top side of the multiwell plate is positioned under the bottom side of the multiwell plate and a rim of a well in the multiwell plate well may be put into contact with cleaning fluid at a corresponding wash well on the wash reservoir, e.g., so the plate well is received by the corresponding wash well on the wash reservoir and residual material is removed at the plate well. A plate well may be received by a corresponding wash well with or without a portion of the plate well entering a volume defined by the wash well (if any). Instead, a wash well may be said to receive a plate well if the plate well is suitably positioned relative to the wash well so that cleaning fluid at the wash well can operate to remove residual material at the plate well.

In another aspect of the invention, an automated system is provided for removing residual material at a plurality of wells of a multiwell plate that each have a rim at an opening to the well. The system may include a wash reservoir that has one or more wash wells each being adapted to receive the rim of a corresponding well of the multiwell plate. A plate manipulator may be included having a gripping element capable of manipulating the multiwell plate so as to invert the multiwell plate and position the plate such that each rim of the plurality of plate wells is simultaneously received by a corresponding wash well on the wash reservoir.

In a further aspect of the invention, an apparatus is presented for removing residual material at a plurality of wells of a multiwell plate that each have a rim. A wash reservoir, having one or more wash wells, may be arranged so that, with the multiwell plate in an inverted position, the rims of the wells located on the multiwell plate are each simultaneously receivable by a corresponding one of the plurality of wash wells. Each wash well may have an inlet that is adapted to provide cleaning fluid to the wash well and/or an outlet to aid in removal of cleaning fluid from the wash well. In one embodiment, each wash well may be formed by a generally flat platform that surrounds a corresponding inlet for the wash well. Cleaning fluid may exit the inlet, and flow over the platform. The wash well platforms may be spaced from each other and extend upwardly from a base, e.g., so that cleaning fluid flows over the platforms and down to the base. Fluid at the base may be collected at one or more outlets.

Other advantages and novel features of the present invention will become apparent from the following detailed description of various non-limiting embodiments of the invention when considered in conjunction with the accompanying figures.

BRIEF DESCRIPTION OF THE DRAWINGS

Aspects of the invention are described with reference to the following drawings in which numerals reference-like elements, and wherein.

DETAILED DESCRIPTION

Aspects of the present invention relate generally to reduction of residual material associated with wells of multiwell sample plates, e.g., used for biological and medically related applications. This invention is not limited in its applications to the details of construction and the arrangement of components set forth in the following description or illustrated in the drawings. The invention is capable of other embodiments and of being practiced or of being carried out in various ways. For example, illustrative embodiments of the invention are described below with reference to use in a multiwell plate handling environment. However, it should be understood that aspects of the invention may be used in systems for any suitable application.

In one aspect of the invention, a method is presented whereby residual material may be removed at a plurality of wells of a multiwell plate. In one embodiment, the method involves providing a multiwell plate that includes a top side where wells are open to fluid transfer in and out, and a bottom side where wells may be closed to fluid transfer. As one of skill in the art will appreciate, wells of a multiwell plate may be used for any suitable purpose, typically a biologically or medically-related research application, where, for example, a reaction may or may not have occurred in a number of the wells. In this regard, reagent and/or other materials may be left over within some of the wells of the multiwell plate. In order to clean the wells, e.g., so that the multiwell plate may be used again or safely discarded, the plate may be substantially emptied by any appropriate method, such as, for example, running a fluid over the upper surface of the multiwell plate, washing material out of the wells, inverting the multiwell plate so that residual material may be dumped from the wells, and/or any combination thereof. After completion of such operations, residual material may still be left over within a number of the wells, and so it may be beneficial to have an approach where cleaning fluid is used to remove residual material from the multiwell plate.

Figure 1:
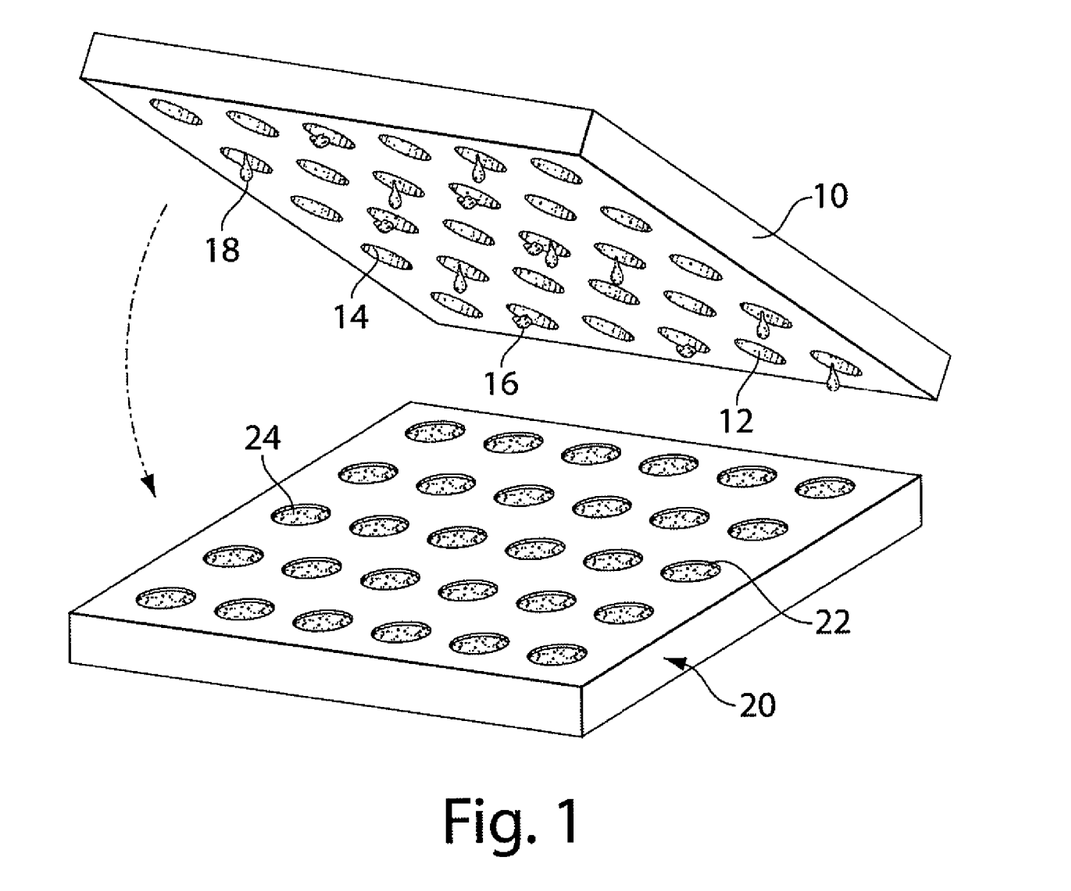
FIG. 1 is a perspective view of a multiwell plate with wells that contain residual material that is to be associated with a wash reservoir in accordance with aspects of the invention.

For example, FIG. 1 shows one illustrative embodiment in which a multiwell plate 10 has been inverted to dump contents of the wells 12 of the plate 10. Despite being inverted, a plurality of the wells 12 may be associated with residual material 14, e.g., the residual material may be located in a variety of areas in relation to the wells 12 such as near the rims or edges of wells 12 and/or at the bottom end of wells 12. The residual material 14 may be in any form such as solid particles 16 lodged or otherwise adhered to portions in or near the wells 12 and/or droplets 18 that may cling near the rims of wells 12 of an inverted multiwell plate 10.

To remove residual material 14 from the plate 10, the plate 10 may be positioned with respect to a wash reservoir 20 so that cleaning fluid 24 may act to remove residual material 14 from the plate 10. For example, the plate 10 may be inverted as shown in FIG. 1 and positioned so that individual wells 12 are received by, e.g., align with and are proximate to, one or more wash wells 22 in the wash reservoir 20. In this embodiment, each well 12 on the multiwell plate 10 corresponds to one wash well 22 on the wash reservoir 20 with the wash wells 22 being slightly larger in diameter than the sample wells 12. However, as discussed in more detail below, it should be understood that the wash wells 22 may be arranged in other suitable ways. Cleaning fluid 24 (in one embodiment, water) in the wash wells 22 may contact the residual material 14 and/or the plate 10 so as to remove the residual material 14. For example, the plate 10 may be lowered so that the top surface of the plate 10 contacts the top surface of the wash reservoir 20 with each of the wells 12 of the plate being in alignment with a corresponding wash well 22. The cleaning fluid 24 may be located in the wash wells 22, e.g., may fill the wells 22 so that the fluid 24 contacts and removes the residual material 14 located at the rims of the plate wells 12. Alternately, or in addition, the cleaning fluid 24 may be injected or otherwise introduced into the interior of the plate wells 12 so as to remove residual material 14 located within wells 12. When removed from the plate 10, the residual material 14 may be associated in any suitable way with the cleaning fluid 24, e.g., may be dissolved into, suspended by, physically knocked off or otherwise carried by the cleaning fluid 24 from the plate 10. It should be understood that usage of the term "remove" with respect to residual material does not necessarily mean complete eradication of residual material from a plate, but also refers to partial or substantial removal, and/or a reduction in concentration of the residual material. Thus, removal of residual material 14 need not result in complete removal of residual material from all portions of a plate 10.

Although FIG. 1 shows a multiwell plate 10 having wells 12 with a circular opening and arranged in a regular array, the multiwell plate 10 may contain wells 12 arranged in any appropriate shape, size, array or other configuration. For example, in some cases, the wells 12 may be arranged in a manner so as to take up an entire row or column in the multiwell plate, e.g., in the form of elongated rectangular wells, as opposed to having multiple, individual wells in rows or columns. In some embodiments, the well shape employed may affect well arrangement on the plate 10, such as where wells are oriented in a concentric fashion. Of course, it will be understood that the wells 12 may take any suitable shape, such as, but not limited to having a rectangular, circular, ellipsoidal, polyhedral or other cross-sectional shape. Moreover, it should be understood that the multiwell plate 10 may have any suitable number of wells 12, such as in the commonly used 48, 96 or 384 well plates, or other numbers of wells. Also, wells 12 need not be arranged in a regular array with wells in rows and columns, but instead may be arranged however desired.

Although the wash reservoir 20 may be provided with a plurality of wash wells 22 arranged to individually correspond with wells 12 on one or more multiwell plates 10, wash wells 22 may be arranged, sized, shaped or otherwise configured in any suitable fashion. For example, in other embodiments, several wells 12 located on a multiwell plate 10 may correspond to a relatively larger wash well 22 of a wash reservoir 20 that may be able to simultaneously remove residual material 14 from the plurality of wells 12 on the multiwell plate 10. Moreover, wash wells 22 may be arranged so that residual material 14 may be simultaneously removed from all wells 12 of a plate 10, as shown in FIG. 1, or may be arranged so that residual material 14 is removed from only a subset of wells 12 (e.g., single wells 12) at any one time. Alignment between plate wells 12 and wash wells 22 may be performed visually, e.g., by a human operator controlling the positioning of a plate 10 relative to a wash reservoir 20, or by an automated system, e.g., by a multi-purpose robot or dedicated plate washing mechanism.

The cleaning fluid 24 provided within each of the wash wells 22 may include any appropriate component or combination of components, including liquid and/or gas. It should be understood that the suitability of cleaning fluid may depend on the type of residual material that is to be removed from the sample wells as certain substances are more prone to react with or otherwise be removed by other particular substances. In some embodiments, the cleaning fluid may be a liquid such as water, which may or may not also be distilled or deionized to any suitable degree. In other embodiments, the cleaning fluid may be or include a liquid such as an acid, a base, any suitable ionic solution, organic solvent, suspension, emulsion, or any combination thereof. In further embodiments, the cleaning fluid may be any suitable gas such as, but not limited to, air, oxygen, nitrogen, carbon dioxide, any noble gas, and/or any inert gas. In yet further embodiments, the cleaning fluid may include solid particles incorporated within a suspension, such as but not limited to soap particles or any appropriate cleaning solid. It should be understood that depending on the residual material to be removed, any combination of the above mentioned substances may be used as a cleaning fluid.

Residual material 14 may be reduced in concentration or otherwise removed in any suitable manner. In some embodiments, bursts of air may be used in removing residual material 14. In other embodiments, liquid may be used to reduce the concentration or otherwise remove residual material 14. In further embodiments, cleaning fluid 24 with appropriate properties or polarity in conjunction with the residual material 14 may be used for removal. Indeed, a combination of the above materials may be used for removing residual material 14 from wells 12 located on a multiwell plate 10. In addition, any suitable treatment scheme may be used such as exposure to particular fluids or combinations thereof for certain time intervals and/or pressure at which fluids are administered at.

In some embodiments of the present invention, when residual material 14 is to be removed from the multiwell plate 10, plate wells 12 and wash wells 22 may contact one another at respective well rims. In other embodiments, plate wells 12 and wash wells 22 need not in contact one another at all, but may be held so as to be in fluid communication with each other. In some embodiments, rims of the wells located on the multiwell plate extend into corresponding wash wells located on the wash reservoir so that spillage of material from one well to another may be minimized. In other embodiments, not all of the wells on the multiwell plate are received by a corresponding wash well, but only a subset of the sample wells located on the multiwell plate, as it is possible that not all sample wells will require removal of residual material. It is possible for the cleaning fluid from the wash wells to flow over the rims of the wash wells and contact wells located on the multiwell plate so as to remove residual material. It can be appreciated that various plate manipulating systems may give rise to varying degrees of precision in positioning the multiwell plate relative to the wash reservoir. In further embodiments, portions of the multiwell plate and portions of the wash reservoir form temporary seals so that cleaning fluid does not leak out from wells located on the multiwell plate and corresponding wash wells.

Figure 2:
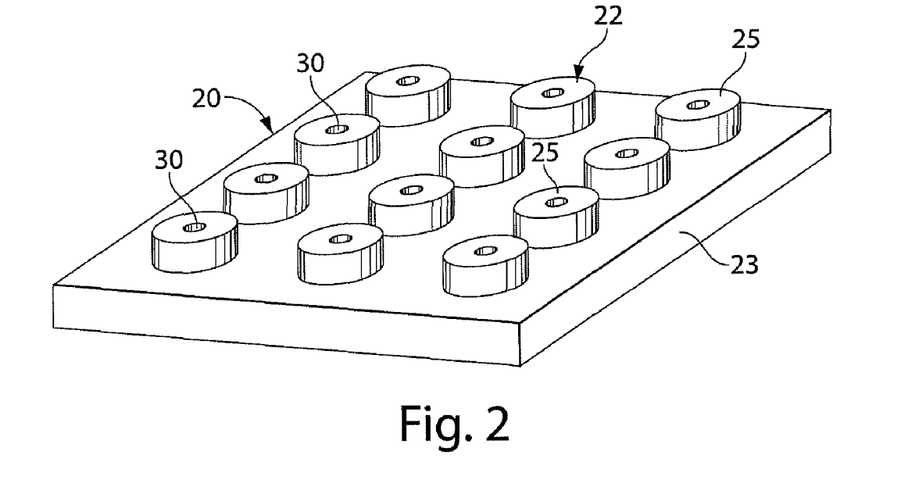
FIG. 2 is a perspective view of a wash reservoir including wash wells with a raised platform in an illustrative embodiment.
Figure 3:
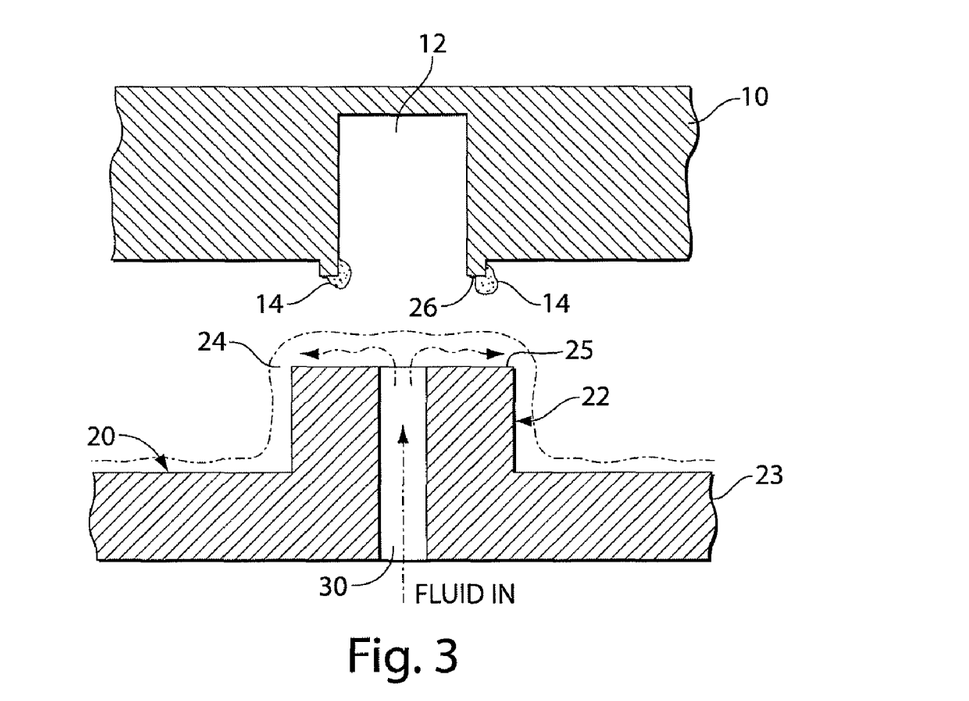
FIG. 3 is a cross-sectional view of a wash well of the FIG. 2 embodiment with a corresponding plate well.

FIG. 2 shows an illustrative embodiment of a wash reservoir 20 with a plurality of wash wells 22 each including a platform 25 that extends from a base 23 of the wash reservoir 20. Each wash well 22 also includes one or more inlets 30 that provide cleaning fluid 24 to the wash well 22. For example, FIG. 3 shows a cross sectional view of a wash well 22 from the FIG. 2 embodiment together with a well plate 10 and plate well 12 positioned over the wash well 22. Cleaning fluid 24 passes through the inlet 30 (e.g., via a suitable conduit in the base 23 of the wash reservoir 20) and flows across the platform 25 of the wash well 22. In this embodiment, the cleaning fluid 24 flows across and down the platform 25 to the base 23, where the fluid 24 may flow to a drain or other suitable outlet. In other embodiments, each wash well 22 may include a corresponding outlet that receives cleaning fluid 24, e.g., an annular opening in the base 23 at the bottom of the wash well 22, or an annular opening in the platform 25 surrounding the inlet 30, may receive cleaning fluid 24 for disposal. Cleaning fluid 24 may be provided to each well 22 at a desired rate, e.g., to form a layer of cleaning fluid 24 that contacts a rim 26 of the plate well 12 (if present) so as to remove material 14 from the plate well 12. As mentioned above, the well plate 10 and the wash reservoir 20 may contact each other (the rim 26 of the plate well 12 may contact the platform 25) or may remain spaced from each other during material 14 removal.

Figure 4:
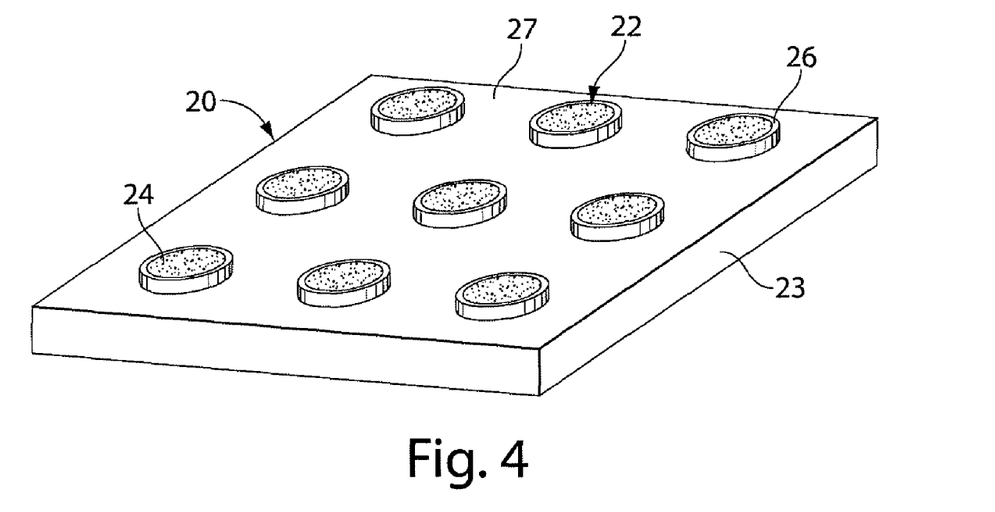
FIG. 4 is a perspective view of a wash reservoir with wash wells having a rim extending above an upper surface of the wash reservoir base in another illustrative embodiment.
Figure 5:
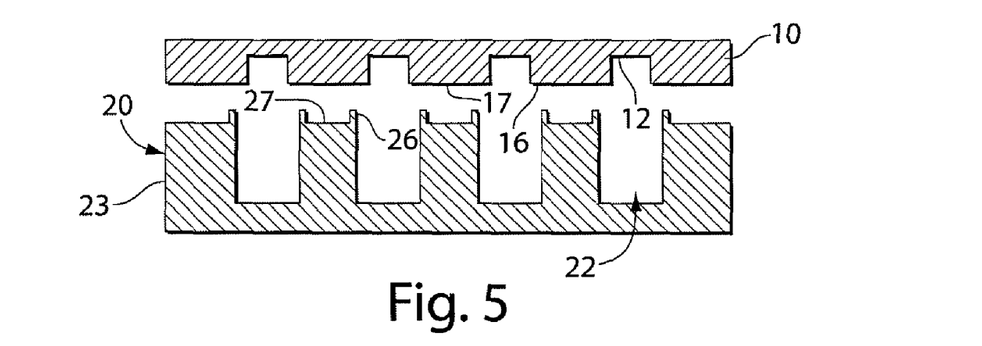
FIG. 5 is a cross-sectional view of the wash reservoir of the FIG. 4 embodiment with a corresponding plate well.
Figure 6:
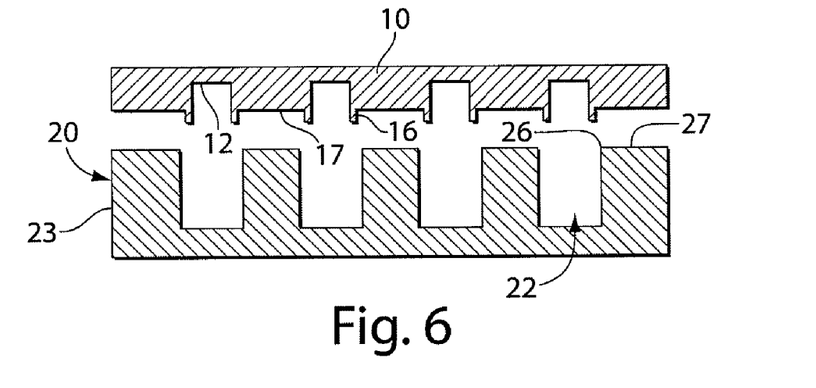
FIG. 6 is cross-sectional view of another wash reservoir with wells having rims flush with an upper surface of the wash reservoir base in another illustrative embodiment.

Other configurations for wash wells 22 and plate wells 12 are possible. For example, FIG. 4 shows an embodiment of a wash reservoir 20 that includes a plurality of wash wells 22 that each include a rim 26 that extends upwardly from an upper surface 27 of the base 23 and surrounds an opening that may receive cleaning fluid 24. FIG. 5 shows a cross sectional view of a wash reservoir 20 with wash wells 22 having an upstanding rim 26 like that in FIG. 4. Cleaning fluid 24 in the wash well 22 may fill the well 22 to the top of the rim 26, and may flow over the rim 26 in some cases, e.g., where an inlet 30 (not shown) provides cleaning fluid 24 to the wash well 22. In this example, a well plate 10 includes plate wells 12 with no rim 16 or other feature that extends from an upper surface 17 of the plate 10. Suitable positioning of the plate 10 relative to the wash reservoir 20 may cause removal of material 14 (not shown in FIG. 5) by cleaning fluid 24 at a corresponding wash well 22. FIG. 6 shows another embodiment in which the wash wells 22 are arranged similarly to that in FIGS. 4 and 5, except that the wash wells 22 do not include an upstanding rim 26. Instead, the upper surface 27 of the base 23 is generally flat and the rims 26 of the wash wells 22 lie in the plane of the upper surface 27. In this embodiment, a corresponding well plate 10 includes plate wells 12 with a rim 16 that extends from the upper surface 17 of the plate 10. The rims 16 for the plate wells 12 may be received at a corresponding wash well 22 (e.g., may extend into a wash well 22) and contact cleaning fluid 24 in the well 22. Such complementary rim arrangements may allow for more effective engagement of the plate well rims 16 with a corresponding wash well 22, thereby allowing for better removal of residual material 14. For example, where a rim 16 of a plate well 12 may be received into a wash well 22 so that a suitable portion of the rim 16 is fully immersed in the cleaning fluid 26, residual material 14 on the rim 16 may be better removed. This type of interlocking arrangement may also help ensure that plate wells 12 are properly aligned with corresponding wash wells 22. For example, if plate well rims 16 are not properly received by respective wash wells 22, a noticeable gap may be present between the plate 10 and the wash reservoir 20, indicating that the plate 10 should be realigned.

Figure 7:
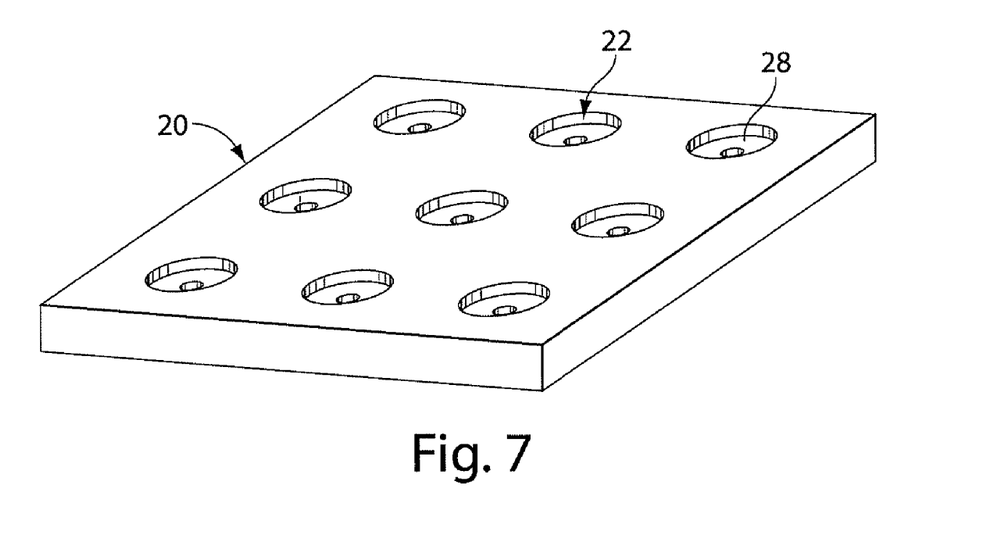
FIG. 7 is a perspective view of a wash reservoir with wash wells having a recessed section around a central opening in another illustrative embodiment.
Figure 8:
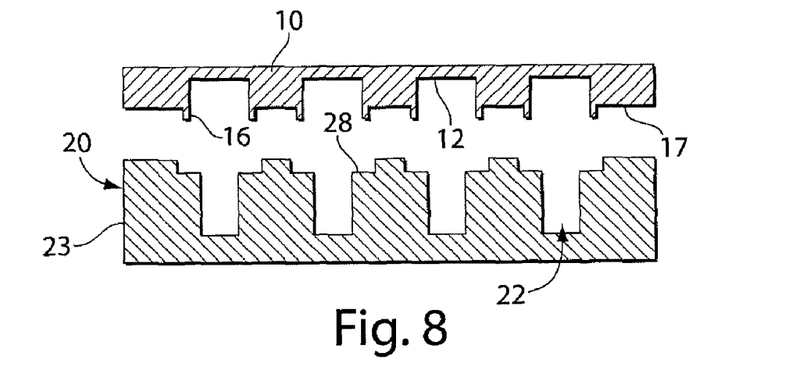
FIG. 8 is a cross-sectional view of the wash reservoir of the FIG. 7 embodiment with a corresponding plate well.
Figure 9:
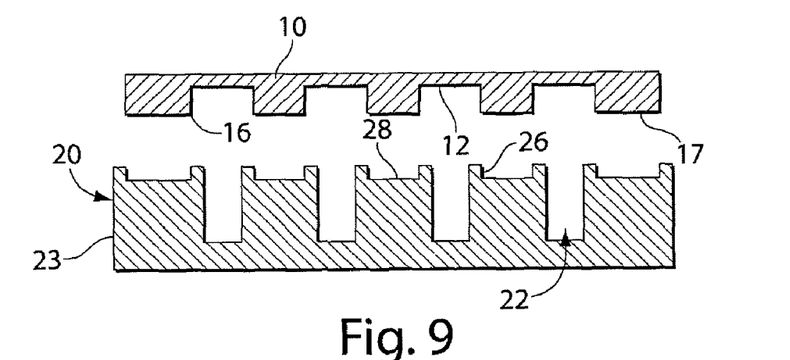
FIG. 9 is a cross-sectional view of an inverted multiwell plate and a wash reservoir where indented regions on the wash reservoir correspond with upper surfaces of the multiwell plate in accordance with aspects of the invention.

FIGS. 7 and 8 show another illustrative embodiment that is similar to FIG. 6, except that the wash wells 22 include an indented, or recessed region 28, instead of a larger, deeper opening in the base 23 of the wash reservoir 20. In this embodiment, rims 16 of the well plate 10 may be seated within indented regions 28 in the wash reservoir 20 so that there is little to no lateral movement between the multiwell plate 10 and the wash reservoir 20. In this regard, if wells 12 on the multiwell plate 10 and wash wells 22 are optimally aligned, lateral movement of wells with respect to one another could make the cleaning process more cumbersome. As a result, some embodiments may incorporate a mechanism for which wells are prevented from substantial movement relative to each other. FIG. 9 shows another similar arrangement, with intended regions 28 of each wash well 22 surrounding, and separated from, a central opening by a rim 26. Thus, rims 16 of the plate wells 12 may be received in indented regions 28. In a converse fashion, those of skill in the art will appreciate that it is also possible for the multiwell plate 10 and the wash reservoir 20 to adopt a reverse configuration where the multiwell plate 10 incorporates an indented region to receive portions of a wash reservoir 20.

Figure 10:
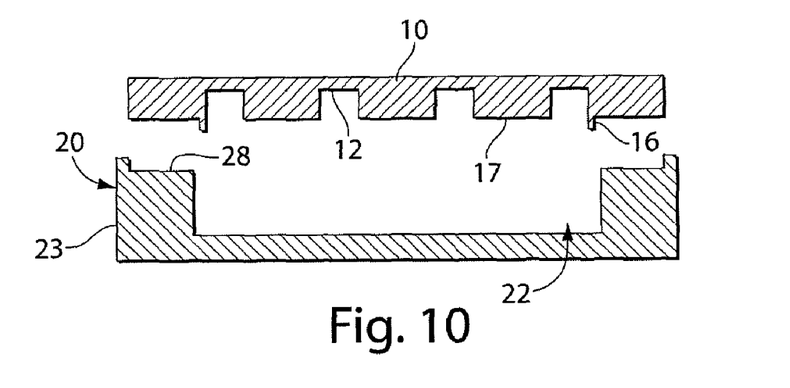
FIG. 10 is yet another cross-sectional view of an inverted multiwell plate and a wash reservoir where a wash well is able to receive multiple plate wells in accordance with aspects of the invention.

FIG. 10 shows yet another illustrative embodiment in which a single larger wash well 22 may receive a plurality of plate wells 12. In this embodiment, an indented region 28 in the wash reservoir 20 may be arranged to receive the upper surface 17 of the multiwell plate 10, but such an arrangement is not required. In this respect, those of skill in the art will appreciate that it is also possible for the multiwell plate 10 and the wash reservoir 20 to adopt a reverse configuration where the multiwell plate 10 adopts an indented region to receive a portion of the wash reservoir 20. In some embodiments, one large wash well 22 may serve to interface with all of the wells 12 located on the multiwell plate 10. In other embodiments, there may be several large wash wells 22 located on the wash reservoir 20 that serve to interface with a subset of wells 12 located on the multiwell plate 10. For example, a wash well 22 on the wash reservoir 20 may interface with a single row of wells located on the multiwell plate 10. In another embodiment, a wash well 22 on the wash reservoir 20 may interface with multiple rows of wells 12 located on the multiwell plate 10.

In another aspect of the present invention, multiwell plate 10 and/or wash reservoir 20 may be purposely agitated during removal of material 14 from a well plate 10. In this respect, a combination of applying cleaning fluid and agitation may aid in loosening residual material 14 in crevices or hard to reach areas in the plate wells 12. For example, in some embodiments, a sonication device may be incorporated in the wash reservoir 20 so that when the reservoir is placed in contact with the multiwell plate 10, sonic waves may travel from the reservoir 20 to the multiwell plate 10, allowing pieces of residual material 14 to be further dislodged. In other embodiments, the multiwell plate 10 may be slightly perturbed in a patterned and/or randomized fashion, vertically and/or laterally, in agitating residual material 14. In further embodiments, the wash reservoir 20 may be slightly perturbed in a patterned and/or randomized fashion, vertically and/or laterally, so that cleaning fluid may be distributed to the multiwell plate 10 in an irregular fashion, allowing for a more thorough wash distribution. In yet more embodiments, the multiwell plate 10 and wash reservoir 20 may be fixed relative to one another and any suitable agitating mechanism, for example those described previously, may be appropriately applied to the two components.

Figure 11:
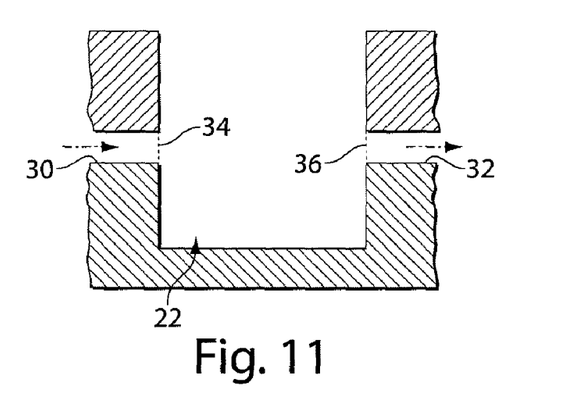
FIG. 11 is a cross-sectional view of a well located on a wash reservoir with an inlet for entrance of cleaning fluid and an outlet for exit of wash well contents in accordance with aspects of the invention.

The cleaning fluid 24 may be provided into wash wells 22 in any suitable way, such as by dispensing via pipette or other dispenser, pouring the fluid into the wells from a pitcher or other container, or other. Alternately, cleaning fluid 24 may be provided by ports associated with wash wells 22 that supply a flow of cleaning fluid to one or more wash wells 22, or remove cleaning fluid from one or more wash wells 22. For example, FIG. 11 shows one embodiment where an inlet 30 provides cleaning fluid 24 through an inlet entrance 34 and an outlet 32 provides an egress for contents of the wash well 22 through an outlet exit 36. It should be understood that in various embodiments of the present invention, the inlet 30 and outlet 32 may be positioned at any appropriate location in the well. In different aspects, the inlet 30 and/or outlet 32 may be ports that take on any suitable cross-sectional shape, serving to channel cleaning fluid in and contents of the wash well 22 out. In some embodiments, the inlet 30 may actively provide cleaning fluid 24 in a pressurized manner to the wash well 22. Similarly, the outlet 32 may actively remove contents from the wash well 22 by providing a negative pressure. In other embodiments, the inlet 30 may provide cleaning fluid 24 in a more passive manner, allowing cleaning fluid to naturally spill in to the wash well 22. In the same fashion, an outlet 32 may allow contents of the wash well 22 to spill out of the wash well 22 through the exit 36. It should be understood that any appropriate number of inlets 30 or outlets 32 may be provided to and/or from the wash well 22.

In another aspect of the present invention, the inlet 30 and/or outlet 32 may include valves that control entrance of cleaning fluid in and exit of contents of the wash well 22 out. There are a wide variety of suitable valves that may control entrance and exit, including, but not limited to, valves that are mechanically or electromechanically actuated. In other embodiments, the inlet 30 and/or outlet 32 may incorporate a membrane or other component that may serve to be fluid permeable or as a filter.

It should be understood that it may also be possible for there to be no defined inlet 30 or outlet 32 built into the wash well 22. In this respect, supply of cleaning fluid may come from over the top opening of the wash well 22 through any appropriate method such as, but not limited to, a supply tube that is suitably placed above the wash well 22 providing cleaning fluid to the well. In this regard, an appropriate supply tube may actively provide pressurized cleaning fluid into the wash well or may provide cleaning fluid in a more passive manner. In addition, exit of contents from the wash well 22 may occur out over the top opening of the wash well 22 through any appropriate method such as, but not limited to, an exit tube that is suitably placed above the wash well 22. An exit tube may actively provide a negative pressure to remove contents from the wash well 22. In another respect, an exit tube may not be required as contents of the wash well 22 may simply spill over the top rim and out of the wash well 22. Once contents spill over the top rim and out of the wash well 22, contents may be collected at the upper surface 27 of the wash reservoir 20 and disposed of together.

Figure 12:
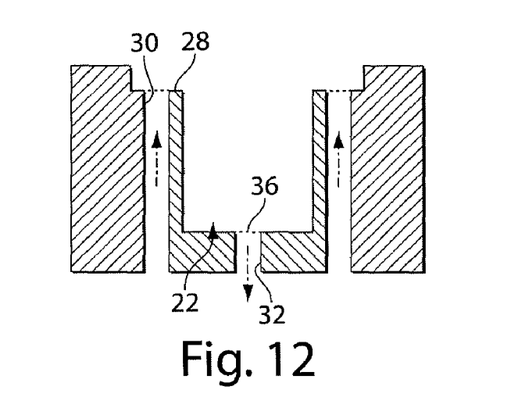
FIG. 12 is another cross-sectional view of a well located on a wash reservoir with an inlet for entrance of cleaning fluid at a recessed region and an outlet for exit of wash well contents at a central opening in accordance with aspects of the invention.

FIG. 12 shows an illustrative embodiment that could be used, for example, in conjunction with the embodiment of FIGS. 7 and 8. That is, cleaning fluid 24 may be provided through one or more inlets 30 within the indented region 28 and contents may be removed through an outlet 32 within the wash well 22. In another embodiment, flow of the cleaning fluid 24 may be reversed from that shown in FIG. 12, with fluid 24 being provided at the outlet 32 and removed at the inlet 30.

Figure 13:
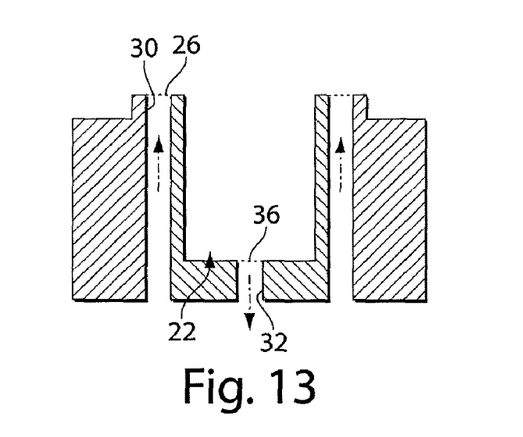
FIG. 13 is another cross-sectional view of a well located on a wash reservoir with an inlet for entrance of cleaning fluid at an upstanding rim and an outlet for exit of wash well contents at a central opening in accordance with aspects of the invention.

FIG. 13 shows another illustrative embodiment that could be used in conjunction with the embodiments in FIG. 2-3, 5 or 9, for example. In this embodiment, cleaning fluid may be provided through inlets 30 at a rim 26 or platform 25 and fluid may be removed through an outlet 32 within the wash well 22. In another embodiment, cleaning fluid 24 flow may be reversed, with fluid 24 being provided at the outlet 32 and removed at the inlet 30.

It should be understood that it is not required for cleaning fluid to be supplied to all of the wash wells in a wash reservoir at once. Rather, cleaning fluid may be distributed suitably as desired. Cleaning fluid may also be exchanged however desired. Cleaning fluid may be provided at any appropriate time interval, for example, intermittent flow, continuous flow, before and/or after cleaning of a well plate, or any other appropriate manner. If cleaning fluid is provided in a non-continuous stream, different cleaning fluids may also be flowed into the wash well through inlet ports. Contents of the wash well may be allowed to exit the wells as well through any suitable arrangement such as, for example, into a drain, or one or more ports that accommodate outflow of fluid. Similar to inflow, outflow may be intermittent or continuous, for example, a wash well may be emptied, partially or fully, via an outlet, and subsequently filled via an inlet. In addition, for some embodiments, inlet and/or outlet ports may be moveable and/or rotatable so that the direction in which cleaning fluid inflow may be suitably adjusted, along with the direction that outflow occurs as well so that washing may be distributed throughout each sample plate 12. In other embodiments, inlet and/or outlet ports may be omni-directional in nature where cleaning fluid can spray out in multiple directions with equal velocity.

Figure 14:
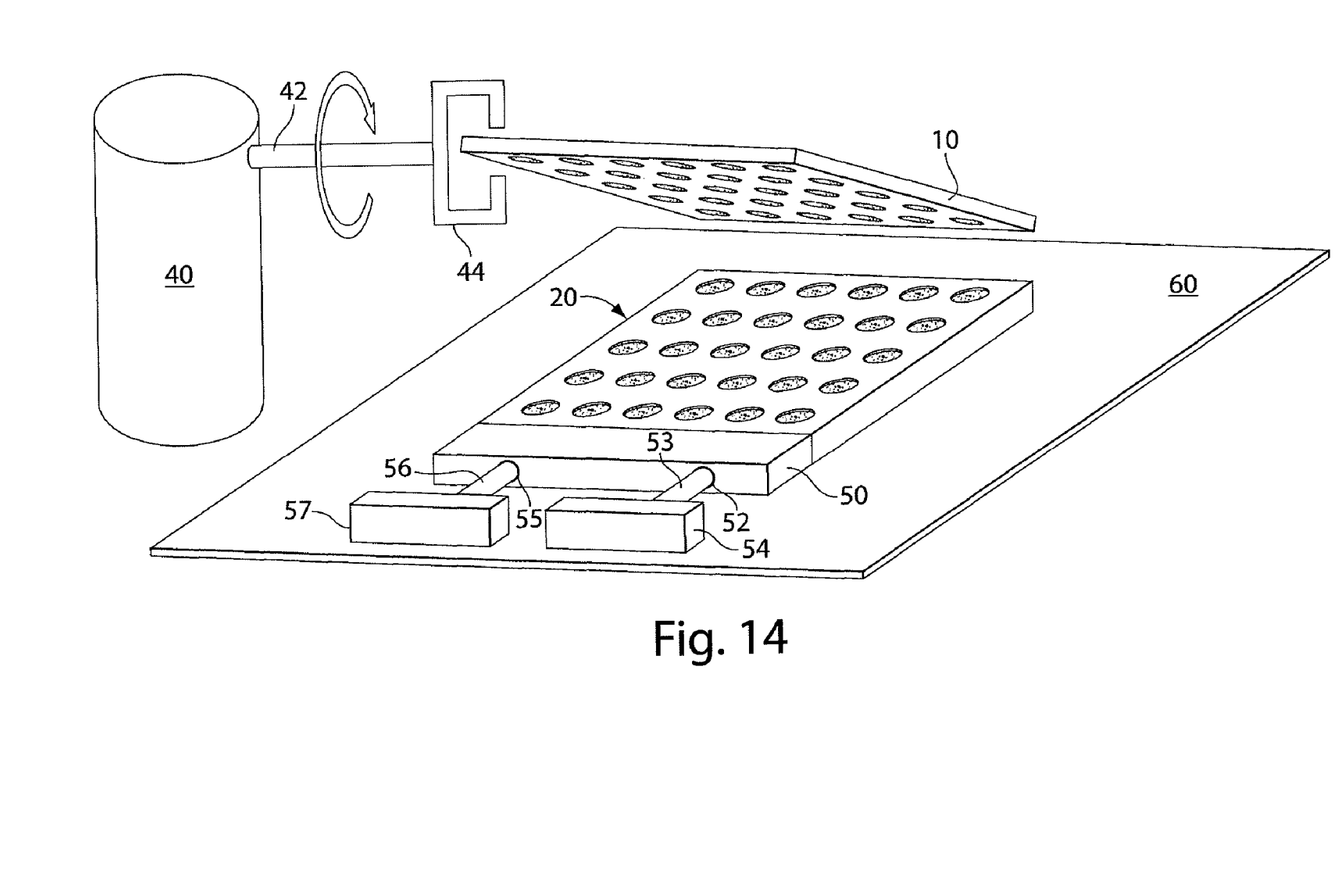
FIG. 14 is a schematic perspective view of an automated system with a manipulator positioning a multiwell plate in association with a wash reservoir in accordance with aspects of the invention.

In accordance with other aspects of the present invention, FIG. 14 depicts one embodiment where an automated system is used for removing residual material from wells of a multiwell plate. In the illustrated embodiment, a plate manipulating robotic system 40 includes a manipulating arm 42 and a gripping mechanism 44 for grasping multiwell plates 10 in an appropriate fashion. A substrate 60 is also depicted, supporting a wash reservoir 20 that also has a wash mechanism 50 connected. The wash mechanism 50 serves to bring cleaning fluid in from a supply source 54, along a supply channel 53, and through a supply port 52. Similarly, the wash mechanism 50 may also serve to remove waste contents out from a waste port 55, along a waste channel 56, and to a waste chamber 57. As will be understood, the wash mechanism 50 may include one or more pumps, tanks, conduits, valves, sensors, controllers, relays, and other components to provide functions for controlling cleaning fluid flow for the wash reservoir 20.

The plate manipulating robotic system 40 equipped with the arm 42 and gripping mechanism 44 shown is a simple schematic, but those of skill in the art will appreciate that any appropriate automated mechanical system would suffice for the purposes presented herein. Indeed, it is possible for the plate manipulating robotic system 40 to have multiple manipulating arms 42 and/or multiple gripping mechanisms 44. The manipulating arm 42 may be generally rotatable and able to translate in any suitable number of degrees of freedom, such as in three independent dimensions. The gripping mechanism 44 attached to the manipulating arm 42 may serve to grasp and release any particular object. In this particular case, the gripping mechanism 44 may grasp a multiwell plate 10. In other embodiments, it is possible for the automated system to be arranged so that the gripping mechanism 44 grasps the wash reservoir 20 and brings the reservoir to the multiwell plate 10. In this regard, the wash reservoir 20 may be inverted with respect to the multiwell plate 10 and cleaning fluid may be provided from wash wells into wells of the multiwell plate 10. As an option, the multiwell plate 10 may then be inverted and/or dried in any suitable fashion. Alternatively, the multiwell plate 10 may be inverted and held in place while the gripping mechanism 44 grasps the wash reservoir 20, bringing the reservoir into association with the multiwell plate 10. In further embodiments, the automated system may be arranged so that multiple gripping mechanisms 44 grasp one or more multiwell plates 10 and/or one or more wash reservoirs 20. In more embodiments, gripping mechanisms may bring multiwell plates and wash reservoirs together without the presence of a substrate support 60. In the illustrative embodiment shown in FIG. 14, the gripping mechanism 44 of the plate manipulating robotic system 40 serves to grasp the multiwell plate 10 and invert the multiwell plate 10 so that the open portions of the sample wells are faced downward or directly toward the open portions of the wash wells located on the wash reservoir. The multiwell plate 10 is then positioned by the plate manipulating system 40, 42, 44 such that each rim of the wells located on the multiwell plate may be relatively simultaneously received by at least one corresponding wash well located on the wash reservoir.

In one example of operation, a multiwell plate 10 with residual material is grasped by a plate manipulating mechanism 40 and inverted so that wells 12 located on the multiwell plate 10 are able to come into alignment with corresponding wash wells 22 on the wash reservoir 20. The plate manipulating mechanism 40 then associates the multiwell plate 10 with the wash reservoir 20 so that sample wells 12 with residual material to be removed are placed in fluid communication with corresponding wash wells 22 on the wash reservoir 20. In some cases, cleaning fluid will be provided through inlet ports 30 within the wash wells 22 and come into contact with residual material located within sample wells 12. As the cleaning process occurs, outlet ports 32 within the wash wells 22 may remove contents resulting from a combination of cleaning fluid and residual material. Cleaning fluid may be sprayed upwardly or otherwise introduced into the multiwell plate wells, or may remain essentially stationary in the wash wells and contact the plate 10 as the plate 10 is positioned proximate the wash reservoir 20.

It should be understood that a number of different types of cleaning fluids may be incorporated at different sequences for different periods of time. Those of skill in the art would appreciate that for every type of residual material, a different combination of cleaning fluid(s) and cleaning times would be required. In this respect, the supply source 54 may provide any combination of cleaning fluid(s) to the wash mechanism 50 which may then supply appropriate cleaning fluid(s) to wash wells 22. To continue, waste contents out of the wash wells 22 may exit through the wash mechanism 50 and eventually enter a waste chamber 57 for subsequent disposal. In some embodiments, fluidic channels and ports may be provided to a wash mechanism 50 for cleaning fluid supply in and waste contents out. In other embodiments, separate wash and waste mechanisms may be used for the residual material removal system. In further embodiments, neither wash nor waste mechanisms may be used for the residual material removal system.

Having described several aspects of this invention, it should be appreciated that various alterations, modifications and improvements will occur to those of skill in the art. Such alterations, modifications and improvements are intended to be part of this disclosure and are intended to be within the spirit and scope of the invention. Thus, the description and drawings herein are intended to be illustrative, not limiting.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for removing residual material at a plurality of sample wells located on a multiwell plate, the multiwell plate having a top side where sample wells are open to receive fluid and a bottom side opposite the top side, the method comprising:
   providing a wash reservoir having a base and a plurality of wash wells arranged to correspond to sample wells of the multiwell plate, each of the wash wells having a corresponding platform supported by and positioned above the base, the platforms being distinct and spaced from each other and each platform having an associated inlet;
   providing a cleaning fluid from a cleaning fluid supply to the inlet associated with each platform of the plurality of wash wells to form a flowing layer of cleaning fluid on each of the platforms;
   inverting the multiwell plate such that the top side of the multiwell plate is positioned under the bottom side of the multiwell plate; and
   contacting a rim of a sample well of the multiwell plate with the flowing layer of cleaning fluid at a corresponding wash well such that material at the rim of the sample well is contacted by the flowing layer of cleaning fluid.

2. The method of claim 1, wherein the step of providing a cleaning fluid comprises introducing the cleaning fluid to a center of each platform of each wash well via the corresponding inlet of the wash well.

3. The method of claim 1, further comprising removing contents from each of the wash wells via one or more corresponding outlets.

4. The method of claim 1, further comprising removing contents from each of the wash wells by allowing contents from each wash well to spill over a top of each wash well.

5. The method of claim 1, wherein the wash reservoir is arranged so that each wash well individually corresponds with and receives a single sample well of the multiwell plate.

6. The method of claim 1, wherein providing a cleaning fluid at each of the plurality of wash wells comprises allowing the cleaning fluid to interact with the residual material so as to dissolve and/or suspend the residual material.

7. An automated system for removing residual material from a plurality of sample wells of a multiwell plate, the sample wells each having a rim at an opening to the sample well, the system comprising:
   a wash reservoir having a base and a plurality of wash wells each adapted to receive the rim of a corresponding well located on the multiwell plate, each of the wash wells having a corresponding platform supported by and positioned above the base, the platforms being distinct and spaced from each other, and each platform having an associated inlet;
   a cleaning fluid supply arranged to supply a cleaning fluid to the platform of each wash well via the associated inlet to create a flowing layer of cleaning fluid that flows over each platform; and
   a plate manipulator having a gripping element arranged to manipulate the multiwell plate to position the multiwell plate in an inverted condition such that each rim of the plurality of sample wells is simultaneously received by a corresponding wash well of the wash reservoir and the rim of each of the plurality of sample wells contacts the flowing layer of cleaning fluid on the platform of the corresponding wash well.

8. The system of claim 7, wherein each wash well further includes an outlet, the outlet being adapted to remove an amount of contents from the wash well.

9. The system of claim 7, wherein each platform surrounds the inlet associated with the platform.

10. The system of claim 7, wherein the wash reservoir is arranged so that each wash well individually corresponds with and receives a single sample well of the multiwell plate.

11. The apparatus of claim 7, wherein the cleaning fluid flows over the platforms down to the base.

* * * * *